United States Patent
Seufert

(10) Patent No.: US 7,206,373 B2
(45) Date of Patent: Apr. 17, 2007

(54) COMPUTED TOMOGRAPHY GANTRY

(75) Inventor: Matthias Seufert, Pettstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/193,860

(22) Filed: Jul. 29, 2005

(65) Prior Publication Data
US 2006/0023833 A1 Feb. 2, 2006

(30) Foreign Application Priority Data
Jul. 30, 2004 (DE) .................. 10 2004 037 076

(51) Int. Cl.
G01N 23/00 (2006.01)

(52) U.S. Cl. .............................. 378/9; 378/4
(58) Field of Classification Search .............. 378/9, 378/4–20
See application file for complete search history.

(56) References Cited

U.S. PATENT DOCUMENTS

| 6,188,747 B1* | 2/2001 | Geus et al. ............ 378/124 |
| 6,229,870 B1 | 5/2001 | Morgan |
| 6,914,959 B2* | 7/2005 | Bailey et al. ............ 378/65 |

FOREIGN PATENT DOCUMENTS

| DE | 31 09 100 A1 | 9/1982 |
| DE | 196 47 626 A1 | 11/1996 |
| EP | 1 570 785 | 9/2005 |
| FR | 2 819 141 | 7/2002 |

* cited by examiner

Primary Examiner—Edward J. Glick
Assistant Examiner—Hoon Song
(74) Attorney, Agent, or Firm—Schiff Hardin LLP

(57) ABSTRACT

To enlarge the angle range to be covered, with a simultaneously smaller variance of the focal spots, in a gantry for a computed tomography at least two x-ray tubes are provided for generation of an x-ray beam instead of a single x-ray tube. The respective x-ray beams of the x-ray tubes cover a defined examination region and a defined region of the detector device in the axial direction of the gantry substantially without overlapping with one another.

6 Claims, 3 Drawing Sheets

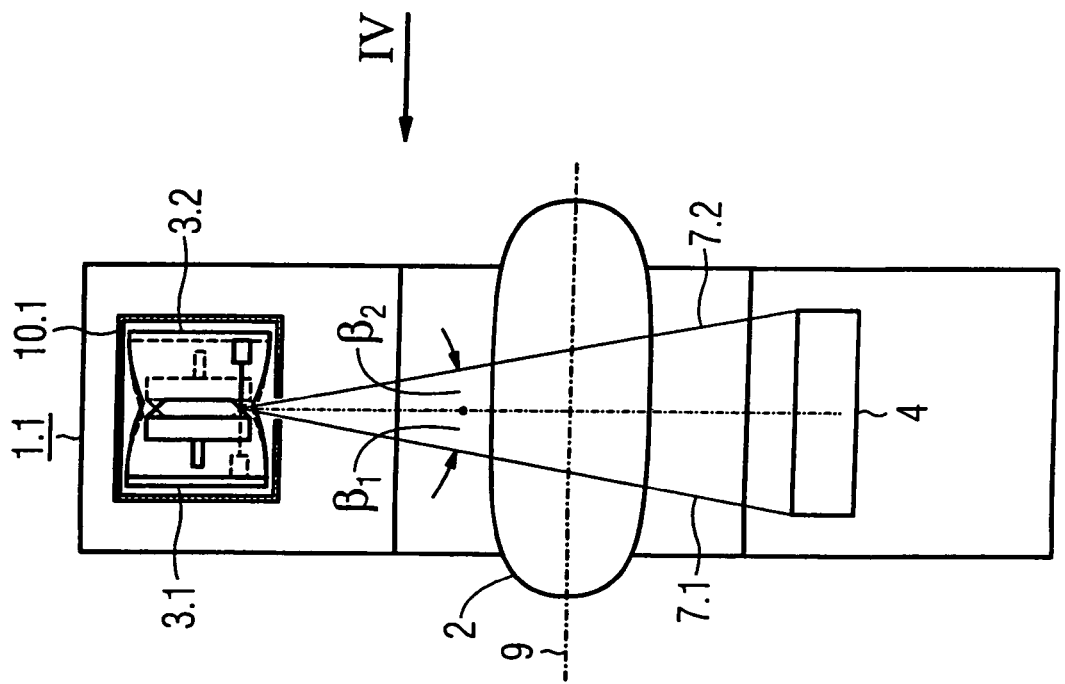
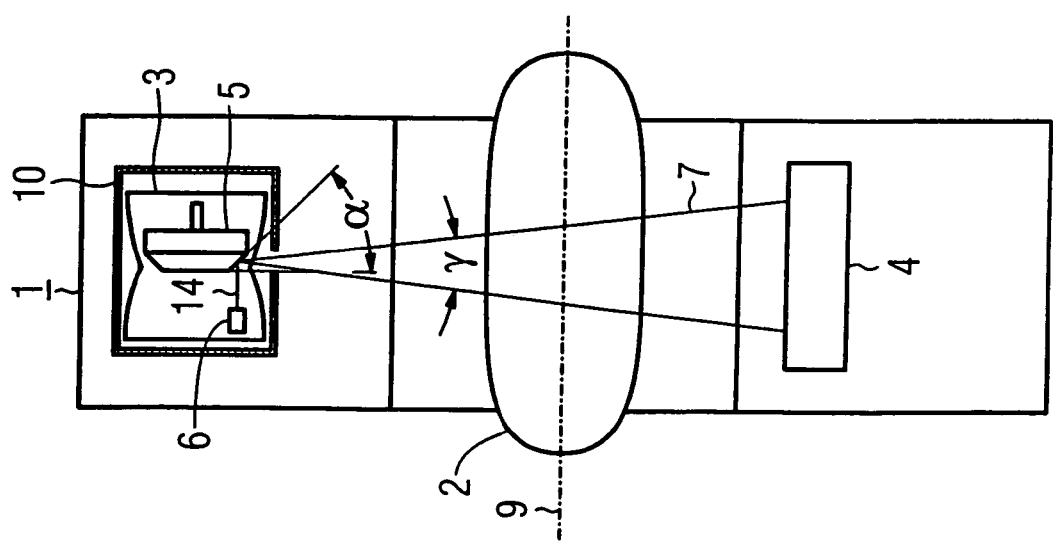

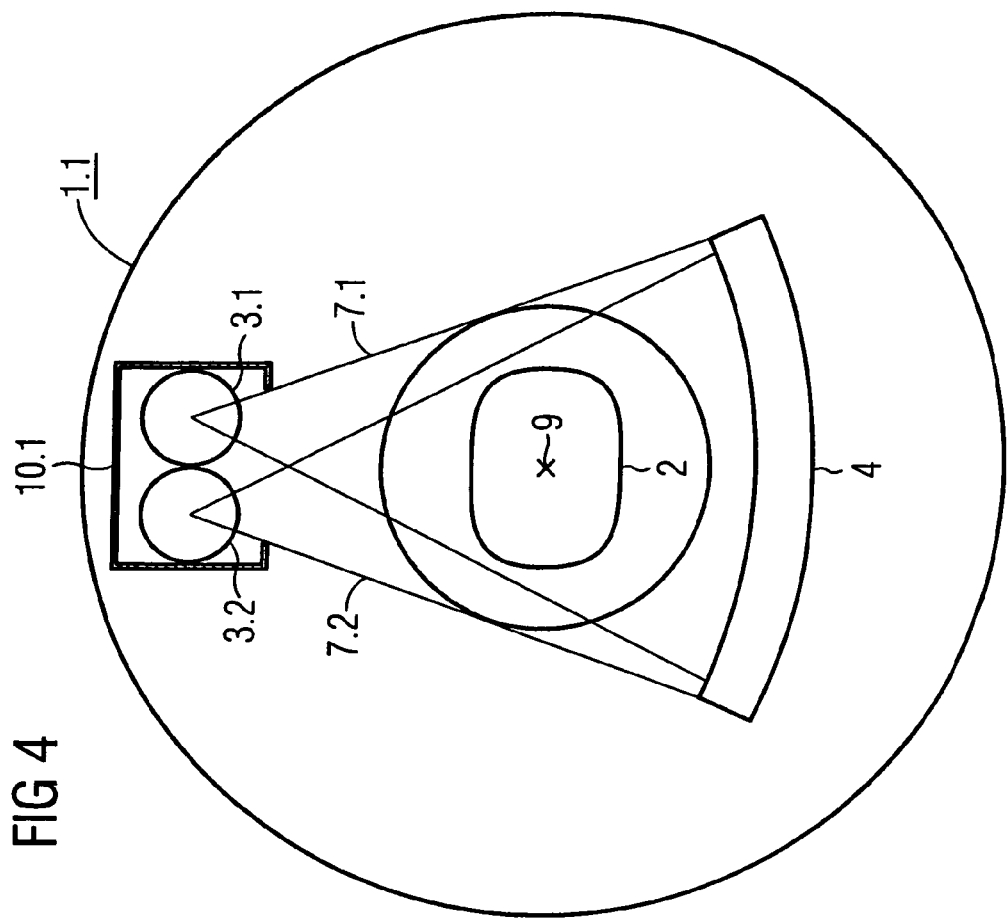
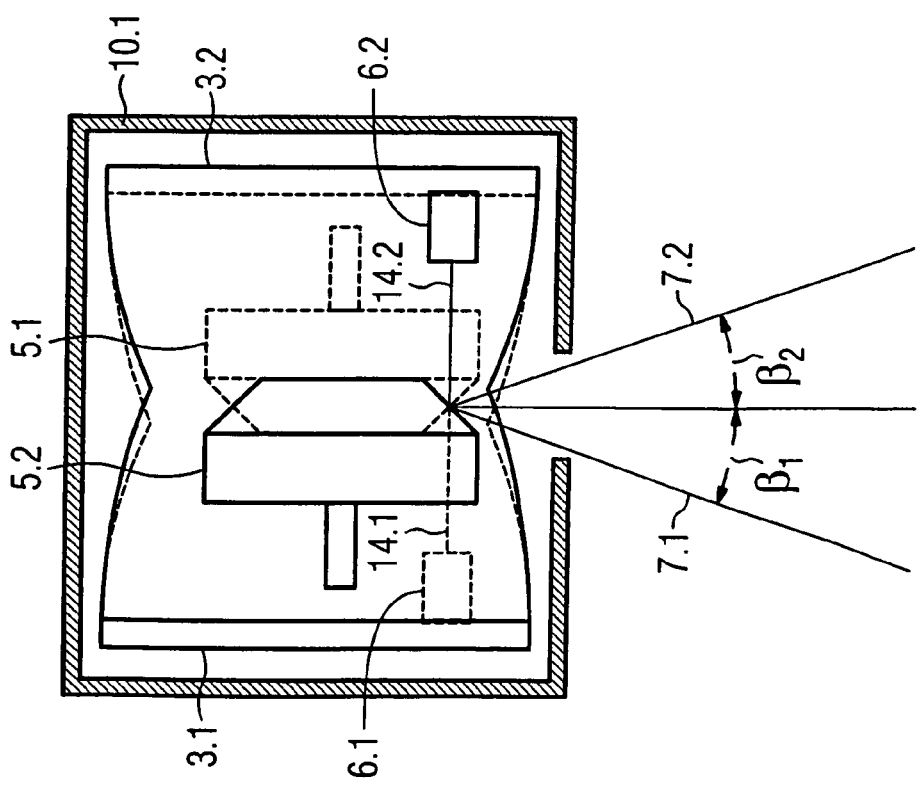

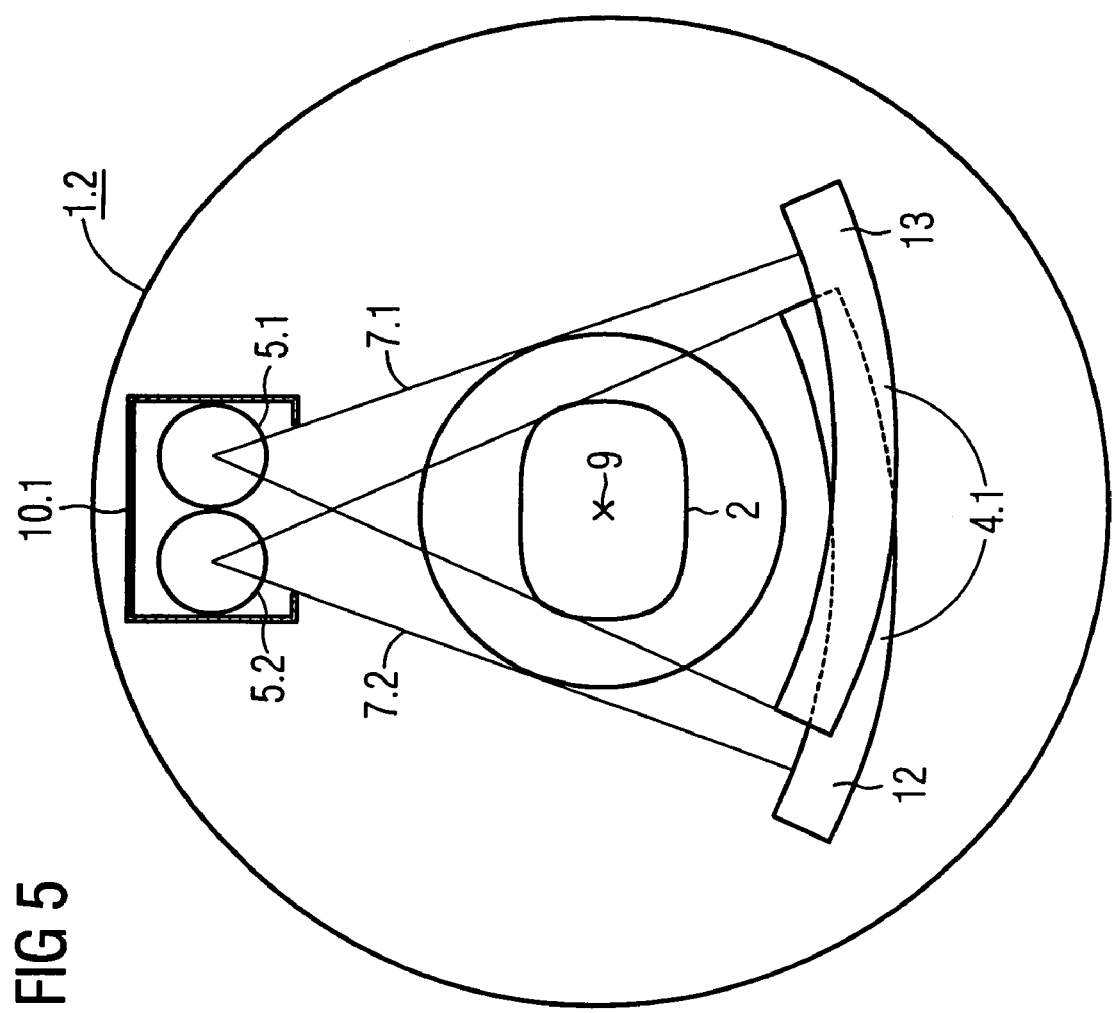

COMPUTED TOMOGRAPHY GANTRY

BACKGROUND OF THE INVENTION

1. Field of the Invention

The invention concerns a gantry, in particular for a computed tomography apparatus of the type generally known from DE 196 47 626 A1.

2. Description of the Prior Art

In such gantries (in particular for computed tomography systems) with a single x-ray tube, the expansion of an x-ray beam (generated by the x-ray tube) with regard to the rotation of the gantry in the axial direction is primarily determined by two factors. First, the anode inclination angle $\alpha$ of the rotatable anode dish of the rotary anode assembly in the x-ray tube limits the maximum angle range that can be covered with sufficient power by the x-ray beam, so that an optimally large anode inclination angle is sought. Second, an anode inclination angle that is too large causes an increased variance of the effective size of the projections of the focal spot in the direction of the image, and can lead to substantial image blurring. Limits are therefore set as to the enlargement of the expansion of the x-ray beam in the axial direction. To increase the x-ray power (which is approximately proportional to the diameter of the anode dish of the x-ray tube), an enlargement of the anode dish would be desirable, but this would require a corresponding enlargement (and available space for such an enlargement) of many components.

SUMMARY OF THE INVENTION

It is an object of the present invention to increase the region to be covered in the axial direction with the x-ray beam in such gantries with as small as possible a variance of the focal spot size.

The above object is achieved in accordance with the principles of the present invention by a computed tomography gantry having an x-ray radiator an a radiation detector mounted thereon, the x-ray radiator generating an x-ray beam that irradiates a defined examination region and a defined region of the radiation detector along an axial direction of the gantry, wherein the radiation detector is formed by at least two x-ray tubes, each x-ray tube generating a tube x-ray beam and the tube x-ray beams in combination irradiating said defined examination region and said defined region of said radiation detector substantially without overlapping with each other.

With the gantry according to the invention, the angle range that can be covered is increased by the use of at least two x-ray tubes without the variance of the size of the projections of the optical focal spot being worsened by a value that would be set if the anode inclination angle were correspondingly increased with a single x-ray tube. By the selection of two x-ray tubes each corresponding to the size of a conventional single x-ray tube, the maximum angle region that can be covered and the x-ray power can be doubled without correspondingly worsening the variance. Conversely, if the coverable angle region remains the same, the variance can be kept small and the image can be improved by the inventive use of at least two x-ray tubes with correspondingly smaller anode inclination angles than a conventional single x-ray tube.

Without changing the x-ray power, a size reduction of the x-ray tube device can additionally be achieved by the selection of smaller x-ray tubes with smaller anode inclination angles, such that a smaller external diameter and/or a larger usable space within the inner diameter is possible for the gantry.

According to an embodiment of the invention, the x-ray tubes are arranged in a common housing, whereby additional space is saved and a more compact arrangement is possible.

To improve the imaging of the region to be irradiated, according to a further embodiment of the invention the detector device has separate detector regions respectively associated with the x-ray tube.

DESCRIPTION OF THE DRAWINGS

FIG. 1 is an axial side view of a known gantry with a single x-ray tube.

FIG. 2 is an axial side view of an inventive gantry with two x-ray tubes that replace the single x-ray tube according to FIG. 1.

FIG. 3 is an enlarged section of the inventive gantry according to FIG. 2.

FIG. 4 shows the inventive gantry according to FIG. 2 in a frontal view.

FIG. 5 shows the inventive gantry according to FIG. 2 with an alternative detector device in a frontal view.

DESCRIPTION OF THE PREFERRED EMBODIMENTS

FIG. 1 shows a gantry 1 of the type known in the prior art for a computed tomography apparatus, with an x-ray tube 3 in a housing 10 and a detector device 4. A subject 2 (in particular a patient) to be examined is positioned in the center of the annular gantry 1. The gantry 1 is mounted such that it can rotate around a central axis 9. The x-ray tube 3 has a cathode 6 and a rotatable anode dish 5 of a rotary anode assembly as the most important components.

In the present example, the anode dish 5 of the rotary anode is canted at an anode inclination angle $\alpha$ in a known manner as a circumferential bevel. The cathode 6 emits an electron beam 14 that, upon its impact on the circumferential bevel of the anode plate 5, generates an x-ray beam 7 directed toward the detector device 4 at an aperture angle $\gamma$. The aforementioned variance results from the size difference between the projections that are defined by the respective outermost rays of the x-ray beam 7 emanating from the focal spot. The x-ray beam 7 covers a defined examination region in which the subject 2 is located. With the aperture angle $\gamma$, the x-ray beam 7 maps (images) on the detector device 4 an axial section of the subject 2 positioned in the opening of the gantry 1. For computed tomography imaging, the gantry 1 rotates around the rotation axis 9 and the subject 2 with the x-ray tube 3 and the detector device 4.

As can be seen from FIG. 2 and (in an enlarged representation) from FIG. 3, in accordance with the invention a first x-ray tube 3.1 and a second x-ray tube 3.2 are provided for generation of the x-ray beam, the first x-ray tube 3.1 being mirrored in the axial direction of the gantry relative to the second x-ray tube 3.2 and the two are offset along their common rotational axis of their respective anodes. The cathodes 6.1; 6.2 respectively emit electron beams 14.1; 14.2 for generation of x-ray beams 7.1; 7.2. The first and second x-ray tubes 3.1 and 3.2 are located in a common housing 10.1.

As shown in the frontal view of FIG. 4, the x-ray beam 7.1 of the first x-ray tube 3.1 borders flush (i.e., with substantially no overlap) with the x-ray beam 7.2 of the second x-ray tube 3.2 in the examination region and in the region of the detector device 4. Together, the x-ray beams 7.1 and 7.2 form the x-ray beam used for a scan that irradiates the defined examination volume and the defined region of the detector device 4 along the axial direction of the gantry. Due to the smaller anode inclination angles (relative to the anode inclination angle α of the individual x-ray tube 3 according to the prior art of FIG. 1) of the two x-ray tubes 3.1 and 3.2, the variance is less given a simultaneously larger total aperture angle β1+β2 of the x-ray beam. According to one embodiment, the two x-ray tubes 3.1 and 3.2 are contained in the common housing 10.1 so that a more compact structural unit is possible. This compactness can be increased so that a common actuation can be used for both anodes. Rotary anodes with planar anode dishes (without a canted bevel) can also be used, allowing the x-ray tubes to be manufactured cost-effectively.

FIG. 5 shows an alternative embodiment of a detector device 4.2 with two detector regions 12 and 13, so that an individual design of the detector regions is possible. Each separate detector region 12 and 13 is arranged or designed so that the respective of foci of the x-ray beams 7.1 and 7.2 generated by the x-ray tubes 3.1 and 3.2 are centered on the detector regions 12 and 13. An equally sharp image thereby results in each region 12 and 13 without increased evaluation outlay.

The invention can be summarized briefly as follows: To enlarge the angle range to be covered with a simultaneously smaller variance of the optical focal spots, in a gantry (in particular for a computed tomography apparatus) at least two x-ray tubes (instead of a conventional single x-ray tube) are provided for generation of an x-ray beam, the x-ray beams of the respective x-ray tubes covering a defined examination region and a defined region of the detector device in the axial direction of the gantry, substantially without overlapping with one another.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography gantry comprising:

a rotatable gantry unit;

an x-ray radiator and a radiation detector mounted on said gantry unit for co-rotation therewith, said x-ray radiator emitting an x-ray beam that irradiates a defined examination region and a defined region of said radiation detector along an axial direction of the gantry unit; and said x-ray radiator comprising at least two x-ray tubes, each of said x-ray tubes generating a tube x-ray beam, said tube x-ray beams respectively irradiating different portions of said defined examination region and different portions of said defined region of said radiation detector without substantially overlapping and, in combination, irradiating all of said defined examination region and all of said defined region of said radiation detector.

2. A computed tomography gantry as claimed in claim 1 wherein the respective tube x-ray beams have edges that are directly adjacent with each other in said examination region and in said region of said radiation detector.

3. A computed tomography gantry as claimed in claim 1 comprising a housing mounted on said gantry unit containing said at least two x-ray tubes.

4. A computed tomography gantry as claimed in claim 1 wherein said at least two x-ray tubes comprise a first x-ray tube and a second x-ray tube, said first and second x-ray tubes being mirror symmetrical with each other with respect to a plane perpendicular to said axial direction.

5. A computed tomography gantry as claimed in claim 1 wherein said radiation detector comprises respective detector regions associated with each of said at least two x-ray tubes, said separate detector regions, in combination, forming said defined region of said radiation detector.

6. A computed tomography gantry as claimed in claim 5 wherein each of said at least two x-ray tubes has a focus from which the tube x-ray beam generated by that x-ray tube is emitted, the respective foci of said at least two x-ray tubes being centered with respect to the respective separate detector regions of said radiation detector.

* * * * *